(12) United States Patent
Rietzel

(10) Patent No.: US 7,679,049 B2
(45) Date of Patent: Mar. 16, 2010

(54) CALIBRATING A POSITRON EMISSION TOMOGRAPHY SCANNER

(75) Inventor: Eike Rietzel, Darmstadt (DE)

(73) Assignee: Siemens Aktiengesellschaft, Munich (DE)

( * ) Notice: Subject to any disclaimer, the term of this patent is extended or adjusted under 35 U.S.C. 154(b) by 7 days.

(21) Appl. No.: 12/110,978

(22) Filed: Apr. 28, 2008

(65) Prior Publication Data

US 2008/0272284 A1 Nov. 6, 2008

(30) Foreign Application Priority Data

May 2, 2007 (DE) .................. 10 2007 020 600

(51) Int. Cl.
*G12B 13/00* (2006.01)
(52) U.S. Cl. .................................................. 250/252.1
(58) Field of Classification Search ............. 250/252.1, 250/363.04
See application file for complete search history.

(56) References Cited

U.S. PATENT DOCUMENTS

| | | | | |
|---|---|---|---|---|
| 4,638,502 | A * | 1/1987 | Yaffe ........................ | 378/207 |
| 6,362,471 | B1 * | 3/2002 | Spitz et al. ............... | 250/252.1 |
| 6,963,065 | B2 * | 11/2005 | Conti et al. ............... | 250/252.1 |
| 2003/0048868 | A1 * | 3/2003 | Bailey et al. ............. | 378/65 |
| 2004/0021065 | A1 | 2/2004 | Weber | |
| 2007/0014391 | A1 * | 1/2007 | Mostafavi et al. ........ | 378/63 |
| 2007/0176087 | A1 * | 8/2007 | Wang et al. .............. | 250/252.1 |
| 2008/0240364 | A1 * | 10/2008 | Main et al. ............... | 378/207 |
| 2008/0273659 | A1 * | 11/2008 | Guertin et al. ........... | 378/65 |

FOREIGN PATENT DOCUMENTS

| DE | 32 08 178 A1 | 9/1983 |
|---|---|---|
| DE | 3208178 | 9/1983 |
| WO | WO 0110301 A1 | 2/2001 |

OTHER PUBLICATIONS

Yasushi Iseki, et al., "Positron camera for range verification of heavy-ion radiotherapy", Nuclear Instruments and Methods in Physics Research A 515 (2003) 840-849.
German Office Action dated Sep. 9, 2008 for DE 10 2007 020 500. 5-52 with English translation.

* cited by examiner

*Primary Examiner*—David P Porta
*Assistant Examiner*—Djura Malevic
(74) *Attorney, Agent, or Firm*—Brinks, Hofer, Gilson & Lione

(57) ABSTRACT

A method for calibrating a positron emission tomography scanner of a radiation therapy device is provided. The method includes applying at least one defined radiation dose in a sample body; measuring the activity generated by the radiation dose using the positron emission tomography scanner; and calibrating the positron emission tomography scanner based on the measured activity.

20 Claims, 3 Drawing Sheets

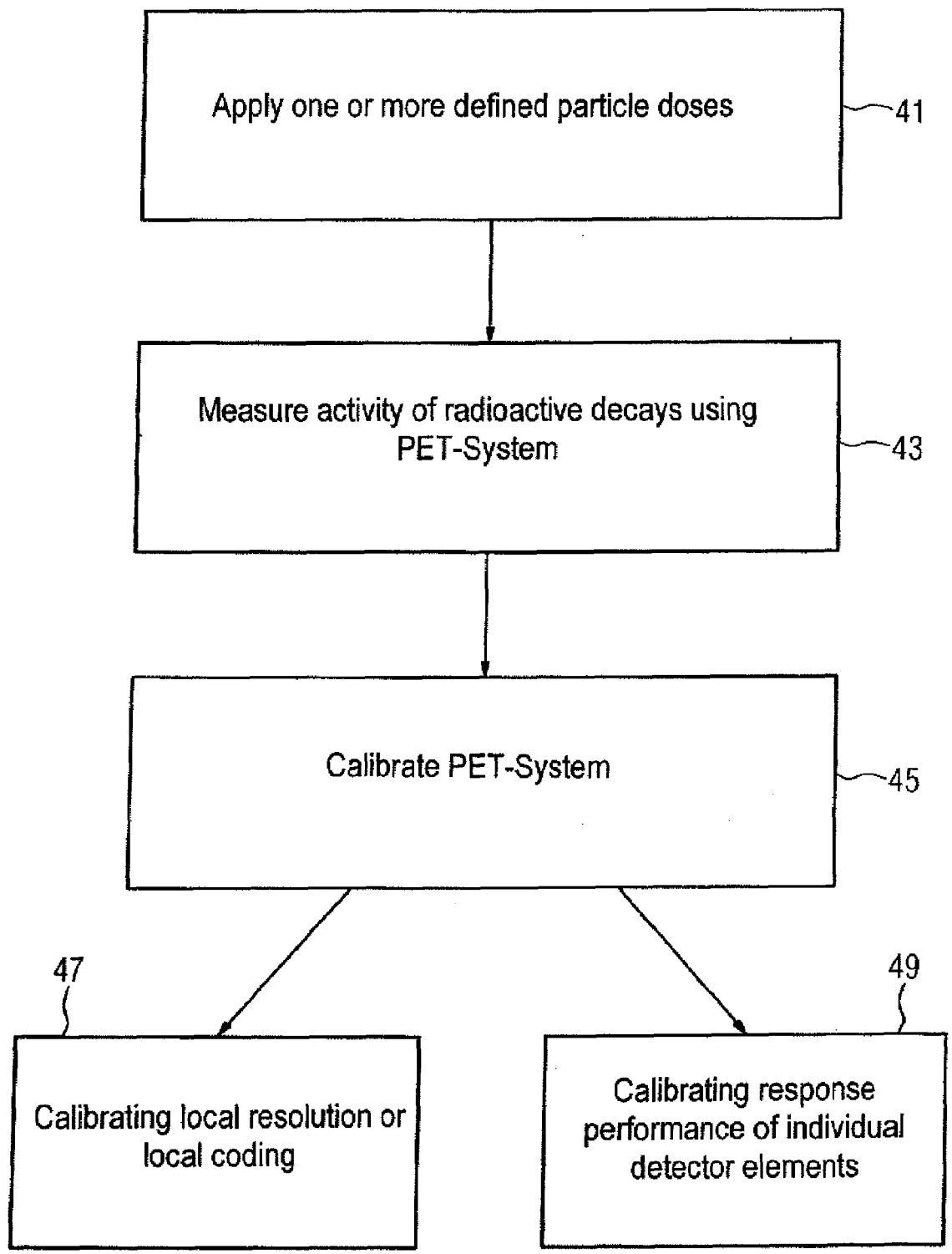

CALIBRATING A POSITRON EMISSION TOMOGRAPHY SCANNER

The present patent document claims the benefit of the filing date of DE 10 2007 020 600.5 filed May 2, 2007, which is hereby incorporated by reference.

BACKGROUND

The present embodiments relate to calibrating a positron emission tomography scanner.

Positron emission tomography (PET) is an imaging method (process) that is used in nuclear medicine and radiation therapy. During PET, a positron is emitted in a body due to radioactive decay. After a short distance, the positron enters into interaction with an electron. The interaction destroys both particles. The destruction creates a pair of gamma quanta. The quanta are at an angle of 180° from one another. The gamma quanta penetrate the body to be examined and after exiting it are recorded by two opposed detectors. A positron emission tomography scanner for imaging includes a plurality of gamma radiation detectors, which surround the patient to be examined. DE 32 08 178 A1 discloses the plurality of gamma radiation detectors being disposed in a ring.

The relevant radioactive decay may be induced, for example, by injection or inhalation of a radioactively marked radiopharmaceutical, such as a tracer. Disease information may be determined based on the spatial distribution of the tracer.

Radioactive decay involving the formation of positrons occurs during radiation therapy from the irradiation of a body, for example, as a function of the radiation dose applied. PET systems may perform such dosage validation or monitoring of the radiation therapy and particle therapy. In particle therapy, measurements are performed in order to check whether the planned radiation dose matches the dose actually applied and/or whether the spatial distribution of an applied dose matches a desired spatial distribution.

PET systems may be used with a particle therapy system and may deviate from the conventional ring form. For example, an in-beam PET system may include only two opposed detectors. The additional opening between the two detectors, for example, may be used to position the patient, or irradiate the patient with a beam passing through this opening without the beam striking the detectors.

To enable precise dosage validation, PET systems are calibrated at certain time intervals, for example, daily. Radioactive sources may be used for calibration. The radioactive sources are disposed in a treatment chamber in which the PET system is also located. The radioactive sources generate a defined activity, which is measured by the PET system. The measurements are used to calibrate the PET system. This process may, for example, include checking an existing calibration of the PET system.

Calibration is complicated, since dedicated radioactive sources have to be set up in the treatment chamber and then removed. This process requires manual intervention, involves cost, and can suffer from errors.

SUMMARY AND DESCRIPTION

The present embodiments may obviate one or more of the drawbacks or limitations inherent in the related art. Calibration of a positron emission tomography scanner of a radiation therapy device may be performed.

In one embodiment, a method for calibrating a positron emission tomography scanner of a radiation therapy device includes applying at least one defined radiation dose in a sample body, at a predetermined location in a treatment chamber; measuring the activity generated by the radiation dose with the positron emission tomography scanner; and calibrating the positron emission tomography scanner based on the measured activity.

In a radiation therapy device, a defined radiation dose may be applied with the treatment beam in a sample body. This is possible since, in a radiation therapy device, the properties of the treatment beam are checked with regard to the precision of the applied dose and the precision of the application site in separate methods. The applied radiation dose generates a defined radioactivity in the sample body that is measured via the positron emission tomography scanner and used for the calibration.

The radiation dose may be applied at a defined site in the treatment chamber, such as at a defined site relative to the positron emission tomography scanner, and/or at a defined site in the sample body. The deflection of a particle beam or the energy of the particle beam may be controlled such that the radiation dose is applied at a defined site in the treatment chamber. Alternatively, the radiation dose may be applied in a phantom and then the phantom is positioned at a defined site in the same or a different chamber.

In one embodiment, the PET system may be calibrated without additional radioactive sources. The intensity of the radiation dose and the application site and/or the application time may be adapted and changed, for example, by controlling the treatment beam.

In one embodiment, a plurality of different radiation doses may be applied in the sample body. The activities generated by the radiation doses are measured with the positron emission tomography scanner. The positron emission tomography scanner is calibrated with the aid of the measured activities.

In one embodiment, the plurality of different radiation doses are different in dose, application site, and/or application time. A calibration can be precisely performed.

In one embodiment, the measured activity or activities may be used to calibrate a response performance of detector elements of the positron emission tomography scanner and/or a local resolution and/or a local coding of the positron emission tomography scanner.

For example, radiation doses that differ in intensity and are applied, for example, successively, may be used for calibrating the response performance of the detector elements.

Radiation doses applied at different sites may be used for calibrating the local resolution or the local coding of the PET system. For example, the defined radiation doses may be distributed in accordance with a predetermined three-dimensional pattern. The local resolution or local coding of the PET system may be precisely calibrated because the measured activity is adapted with the predetermined three-dimensional pattern. From the three-dimensional pattern, additional information may be obtained about the spatial distribution of the induced radioactivity. The additional information may be used for calibrating the PET system.

The sample body may, for example, be a solid-state phantom, a polymethylmethacrylate (PMMA) phantom or some other phantom.

The method for calibrating a radiation therapy device may be provided where the radiation therapy device is a particle therapy system. A particle dose applied by the particle beam is the defined radiation dose.

The radiation therapy device, such as a particle therapy system, may include a positron emission tomography scanner in a treatment chamber. The radiation therapy device or positron emission tomography scanner may perform a calibration method.

BRIEF DESCRIPTION OF THE DRAWINGS

FIG. 4 illustrates a diagram of a method for calibrating a positron emission tomography scanner.

DETAILED DESCRIPTION

Figure 1:
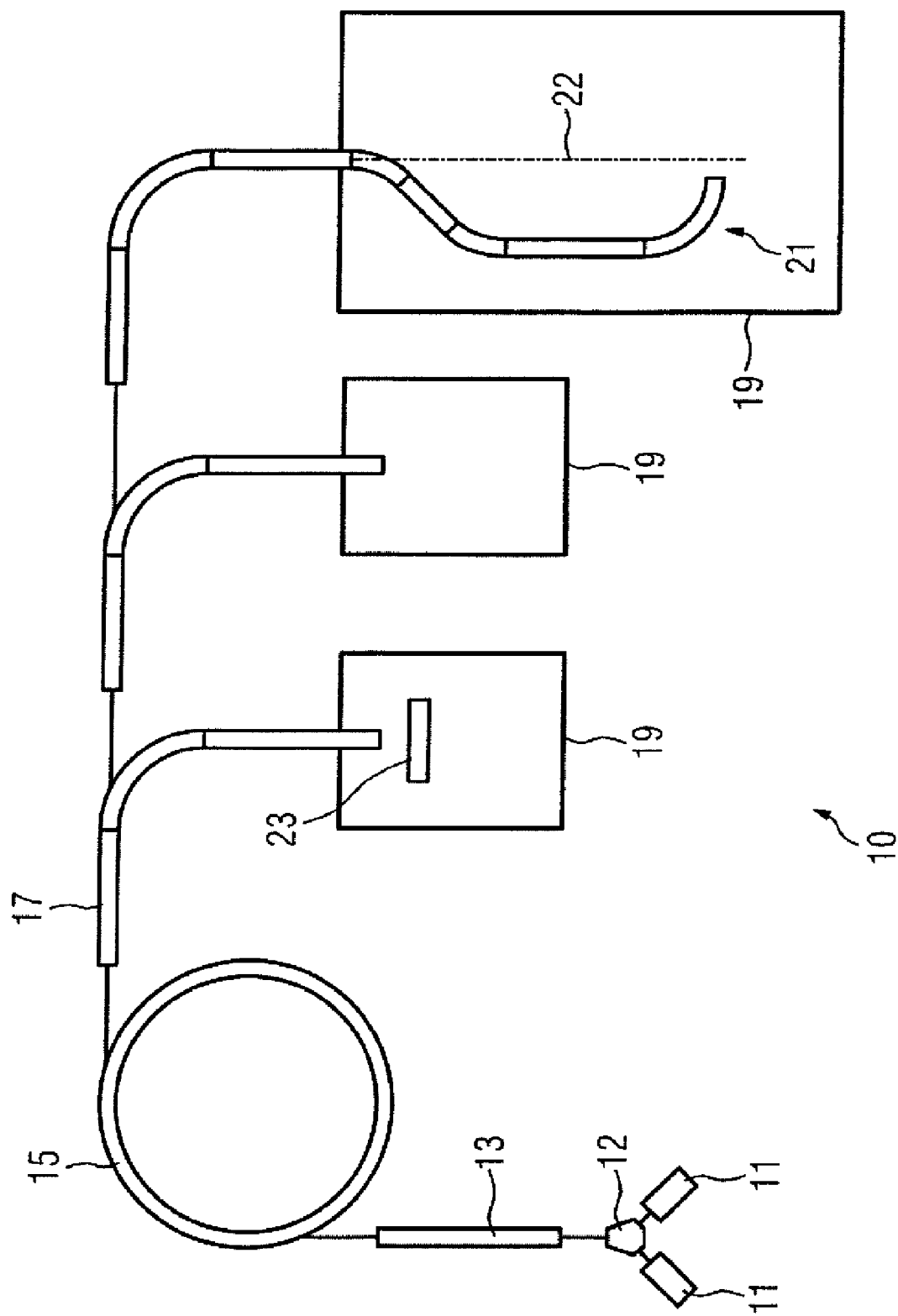
FIG. 1 illustrates one embodiment of a particle therapy system.

FIG. 1 shows a particle therapy system 10. The particle therapy system 10 may irradiate a body, such as tissue diseased with a tumor or tumors, with a particle beam.

The particles may be ions, such as protons, pions, helium ions, carbon ions, or other types of ions. The particles may be generated in a particle source 11. As shown in FIG. 1, there may be two particle sources 11 that generate two different types of ions. A switchover may be made between the two types of ions within a short time. A switching magnet 12 may be used for the switchover. The switching magnet 12 is located between the ion sources 11 and a preaccelerator 13. For example, the particle therapy system 10 may operate simultaneously with protons and carbon ions.

The ions generated by the ion source or one of the ion sources 11 and optionally selected with the switching magnet 12 are accelerated to a first energy level in the preaccelerator 13. The preaccelerator 13 is, for example, a linear accelerator (LINAC, for "LINear ACcelerator"). The particles are fed into an accelerator 15, such as a synchrotron or cyclotron. In the accelerator 15, they are accelerated to high energies for the irradiation. Once the particles exit from the accelerator 15, a high-energy-beam transport system 17 carries the particle beam to one or more treatment chambers 19. In a treatment chamber 19, the accelerated particles are aimed at a body to be irradiated. The accelerated particles may be aimed at a body from a fixed direction (e.g., in a "fixed-beam" chamber) or from various directions via a rotatable gantry 21 that is movable about an axis 22.

The exemplary embodiments described below may be used both in conjunction with the particle therapy system shown in FIG. 1 and with other particle therapy systems or radiation therapy systems.

Figure 2:
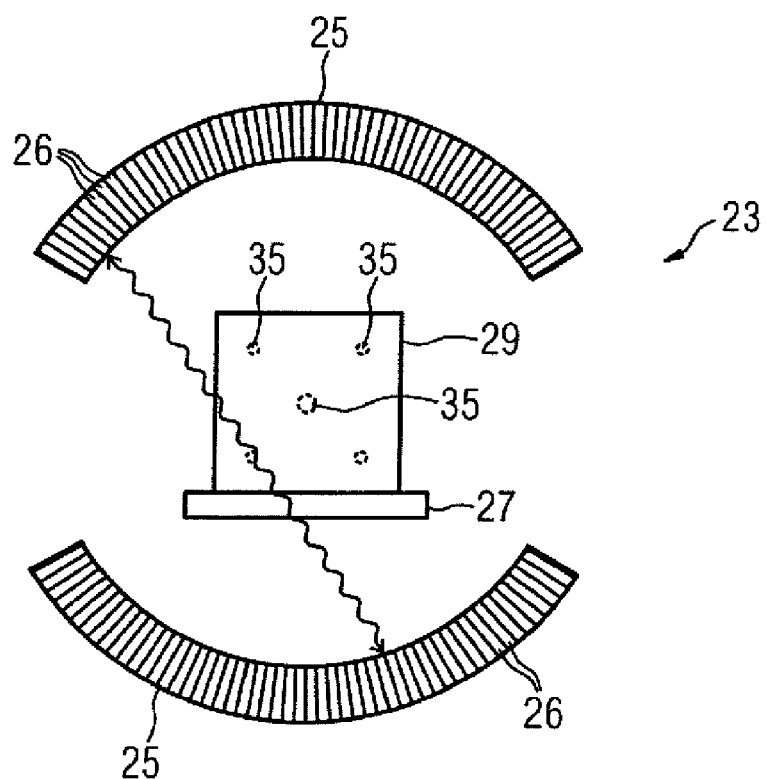
FIG. 2 illustrates one embodiment of a positron emission tomography scanner in a treatment chamber of a particle therapy system.
Figure 3:
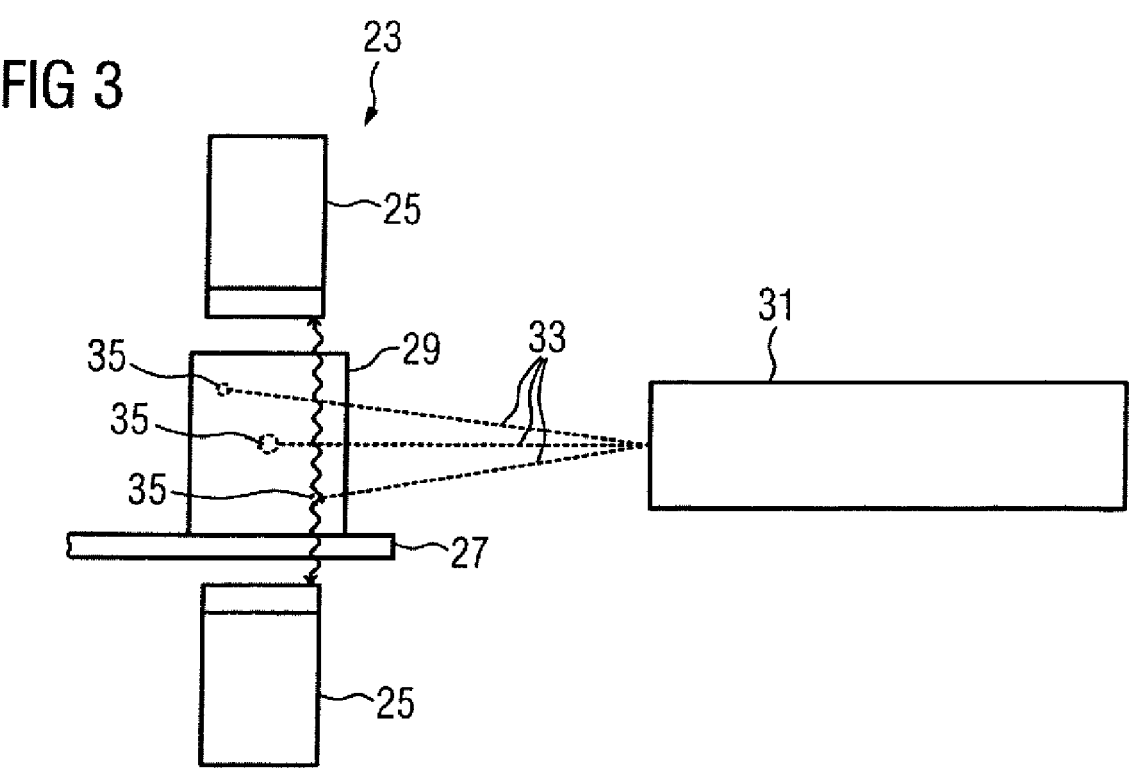
FIG. 3 illustrates the positron emission tomography scanner.

In one embodiment, a treatment chamber 19 may include a PET system 23. The PET system 23 may validate or monitor dosage during an irradiation session in the course of the particle therapy. FIGS. 2 and 3 show a PET system 23, which may be calibrated using a sample body, as described below.

FIG. 2 shows a PET system 23 with a ring-shaped structure. The detector ring, for example, includes two opposed ring segments 25. A plurality of detector elements 26 may be arranged on the two opposed ring segments 25. The detector ring may be used to position a horizontal treatment table, for example, both perpendicular to and along the plane of the detector ring.

For calibrating the PET system 23, a sample body 29 is located in the center of the detector ring, on a tabletop 27 of a treatment table. The sample body, for example, may be a block-shaped PMMA phantom.

FIG. 3 illustrates a ringlike PET system 23 with the sample body 29. As shown in FIG. 3, the particle therapy system may include a beam exit 31. The particle beam 33 may exit a treatment or irradiation chamber from the beam exit 31. The beam exit 31 may be used to aim the particle beam 33 at one or more different areas in the sample body 29.

One or more defined particle doses 35, distributed in a three-dimensional pattern, may be applied in the sample body 29. The intensities of the particle doses 35 are illustrated by circles of different sizes in FIGS. 2 and 3. The individual particle doses 35 may be applied successively in the sample body.

The particle therapy system may include a control unit that controls the particle beam 33 and the applied particle doses 35. The control unit may control deflector magnets, for example, for deflecting the particle beam 33. The particle beam energy may be adapted for controlling the penetration depth of the particle beam in the sample body.

The applied particle doses 35 induce a defined radioactivity in the sample body 29. The radioactivity is detected with the aid of the PET system 23. Because of the defined particle dose or particle doses 35, the induced activity is known, calibration of the PET system 23 may be accomplished.

A calibration of the PET system 23 may be performed with a single particle dose, since the three-dimensional information may be correlated with the measured activities by the distribution pattern. For example, redundant calibration of the PET system 23 may be done. Particle doses 35 that have been applied according to a three-dimensional pattern may be used to calibrate the local resolution of the PET system 23. The three-dimensional pattern may be matched to the measured activity of the PET system 23.

Particle doses 35 applied in succession and differing in intensity may be used for calibrating the response performance of individual detector elements 26.

Although in FIGS. 2 and 3 the calibration is described for a particle beam that may be scanned actively, the calibration may be used in passive beam application, for example, beam application in which the treatment beam is shaped by passive elements in the beam course.

FIG. 4 illustrates a diagram of the method used to calibrate a positron emission tomography scanner.

In act 41, one or more defined particle doses are applied, with the aid of the particle beam of the particle therapy system, in a sample body placed relative to the PET system. In the sample body, the particle dose or doses applied induce radioactive decays, whose activity is measured using the PET system in act 43. In act 45, the PET system is calibrated, using (as a function of) the measured radioactivity. The calibration may be done, for example, directly from the measured data. For the calibration, a reconstruction of a PET image may be done with the raw data. The image may be used for the calibration.

In the calibration, a local resolution or local coding of the PET system may, for example, be calibrated in act 47, or, depending on the design of the method, the response performance of individual detector elements may be calibrated in act 49.

Although in the drawings the method has been described in terms of particle therapy, the method may be employed in conventional radiation therapy, for example, using X-rays.

The invention claimed is:

1. A method for calibrating a positron emission tomography scanner of a radiation therapy device, the method comprising:

applying, using a radiotherapy device, at least one defined radiation dose in a sample body to induce a defined activity in the sample body, the at least one defined radiation dose being applied by irradiating the sample body with a treatment radiation beam of the radiotherapy device;

measuring the activity generated by the at least one defined radiation dose with the positron emission tomography scanner; and calibrating the positron emission tomography scanner as a function of the measured activity.

2. The method as defined by claim 1, wherein applying at least one defined radiation dose includes applying the at least one defined radiation dose at a predetermined site in a treatment chamber and/or in the sample body.

3. The method as defined by claim 2,
wherein applying at least one defined radiation dose includes applying a plurality of different radiation doses in the sample body;
wherein measuring the activity generated by the at least one defined radiation dose includes measuring the activities generated by the plurality of different radiation doses with the positron emission tomography scanner;
wherein calibrating the positron emission tomography scanner includes calibrating the positron emission tomography scanner as a function of the measured activities.

4. The method as defined by claim 3, wherein the plurality of different radiation doses are different in dose, application site, application time, or combinations thereof.

5. The method as defined by claim 2, wherein calibrating comprises calibrating a response performance of detector elements of the positron emission tomography scanner, a local resolution, a local coding of the positron emission tomography scanner, or combinations thereof as a function of the measured activity.

6. The method as defined by claim 2, wherein the sample body is a polymethylmethacrylate phantom.

7. The method as defined by claim 2, wherein the radiation therapy device is a particle therapy system, with which at least one defined particle dose is applied as a defined radiation dose in the sample body.

8. The method as defined by claim 1, wherein applying at least one defined radiation dose includes applying a plurality of different radiation doses in the sample body.

9. The method as defined by claim 8, wherein the plurality of different radiation doses are different in dose, application site, or application time, or combinations thereof.

10. The method as defined by claim 1, wherein calibrating comprises calibrating a response performance of detector elements of the positron emission tomography scanner, a local resolution, a local coding of the positron emission tomography scanner, or combinations thereof as a function of the measured activity.

11. The method as defined by claim 1, wherein the sample body is a polymethylmethacrylate phantom.

12. The method as defined by claim 1, wherein the radiation therapy device is a particle therapy system, with which at least one defined particle dose is applied as one of the at least one defined radiation dose in the sample body.

13. The method as defined by claim 1,
wherein applying at least one defined radiation dose includes applying a plurality of different radiation doses in the sample body;
wherein measuring the activity generated by the at least one defined radiation dose includes measuring the activities generated by the plurality of different radiation doses with the positron emission tomography scanner;
wherein calibrating the positron emission tomography scanner includes calibrating the positron emission tomography scanner as a function of the measured activities.

14. The method as defined by claim 1, wherein applying at least one radiation dose includes distributing the at least one defined radiation dose in accordance with a predetermined three-dimensional radiation pattern.

15. The method as defined by claim 14, wherein measuring includes obtaining a spatial distribution of the induced activity using the predetermined three-dimensional radiation pattern.

16. The method as defined by claim 1, wherein applying includes successively applying defined radiation doses that differ in intensity.

17. The method as defined by claim 1, wherein calibrating the positron emission tomography scanner includes calibrating the positron emission tomography scanner as a function of the measured activity and a known activity known from the defined at least one radiation dose, the measured activity being correlated with the known activity.

18. A radiation therapy device, comprising:
a radiation source that is operable to apply at least one defined radiation dose in a sample body, the at least one defined radiation dose being applied by irradiating the sample body with a treatment radiation beam, the defined radiation dose inducing a defined activity in the sample body;
a positron emission tomography scanner in at least one treatment chamber, the positron emission tomography scanner being operable to measure radiation activity generated by the at least on defined radiation dose; and
a control unit that is operable to calibrate the positron emission tomography scanner based on measured radiation activity.

19. The radiation therapy device as claimed in claim 18, wherein the radiation source is a particle source.

20. The radiation therapy device as claimed in claim 18, wherein the at least one defined radiation dose is a plurality of different dosages.

* * * * *